United States Patent
Sandahl

(10) Patent No.: US 9,364,348 B2
(45) Date of Patent: Jun. 14, 2016

(54) VACUUM SUSPENSION SYSTEM

(71) Applicant: OSSUR HF, Reykjavik (IS)

(72) Inventor: David Sandahl, Seltjarnarnes (IS)

(73) Assignee: OSSUR HF, Reykjavik (IS)

( * ) Notice: Subject to any disclaimer, the term of this patent is extended or adjusted under 35 U.S.C. 154(b) by 18 days.

(21) Appl. No.: 14/192,949

(22) Filed: Feb. 28, 2014

(65) Prior Publication Data

US 2014/0249648 A1 Sep. 4, 2014

Related U.S. Application Data

(60) Provisional application No. 61/771,190, filed on Mar. 1, 2013.

(51) Int. Cl.
| | | |
|---|---|---|
| *A61F 2/80* | (2006.01) | |
| *A61F 2/68* | (2006.01) | |
| *A61F 2/74* | (2006.01) | |

(52) U.S. Cl.
CPC ... *A61F 2/80* (2013.01); *A61F 2/68* (2013.01); *A61F 2002/742* (2013.01); *A61F 2002/802* (2013.01); *A61F 2002/805* (2013.01)

(58) Field of Classification Search
CPC .............. A61F 2002/742; A61F 2002/802; A61F 2002/805; A61F 2/80
See application file for complete search history.

(56) References Cited

U.S. PATENT DOCUMENTS

| | | |
|---|---|---|
| 708,685 A | 9/1902 | White |
| 980,457 A | 1/1911 | Toles |
| 1,288,803 A | 12/1918 | Beck |
| 1,586,015 A | 5/1926 | Underwood |
| 2,424,278 A | 7/1947 | Kunkel |
| 2,464,443 A | 3/1949 | Ganoe et al. |
| 2,530,285 A | 11/1950 | Catranis |
| 2,533,404 A | 12/1950 | Sharp et al. |
| 2,606,325 A | 8/1952 | Nielson et al. |

(Continued)

FOREIGN PATENT DOCUMENTS

| | | |
|---|---|---|
| AU | 670631 B2 | 7/1996 |
| BE | 675386 A | 5/1966 |

(Continued)

OTHER PUBLICATIONS

International Search Report and Written Opinion of the International Searching Authority from International Application No. PCT/US2014/019218, mailed May 9, 2014.

(Continued)

*Primary Examiner* — Bruce E Snow
(74) *Attorney, Agent, or Firm* — Workman Nydegger

(57) ABSTRACT

A vacuum suspension system includes a rigid socket defining a socket wall having exterior and interior surfaces. The socket defines an aperture extending between the exterior and interior surfaces, and has a closed distal end and an open proximal end with an interior cavity defined by the interior surface. A fluid regulator is provided at the aperture and operatively engages the fluid regulator. A pump system includes a pump and a covering for securing over the exterior surface of the socket and carrying the pump. The pump is configured for placement proximate to the fluid regulator and arranged for drawing air from the socket through the aperture. A chamber having a variable volume is formed by a space defined between the exterior surface and an inner surface of the covering proximate to the pump.

10 Claims, 7 Drawing Sheets

(56) References Cited

U.S. PATENT DOCUMENTS

| | | |
|---|---|---|
| 2,664,572 A | 1/1954 | Blevens |
| 2,671,225 A | 3/1954 | Schoene et al. |
| 2,696,010 A | 12/1954 | Robinson |
| 2,696,011 A | 12/1954 | Galdik |
| 2,790,180 A | 4/1957 | Hauser |
| 2,808,593 A | 10/1957 | Anderson |
| 3,253,600 A | 5/1966 | Scholl |
| 3,322,873 A | 5/1967 | Hitchcock |
| 3,377,416 A | 4/1968 | Kandel |
| 3,557,387 A | 1/1971 | Ohlenbusch et al. |
| 3,631,542 A | 1/1972 | Potter |
| 3,712,298 A | 1/1973 | Snowdon et al. |
| 3,732,578 A | 5/1973 | Pollack |
| 3,751,733 A | 8/1973 | Fletcher et al. |
| 3,806,958 A | 4/1974 | Gusev |
| 3,858,379 A | 1/1975 | Graves et al. |
| 3,889,301 A | 6/1975 | Bonner, Sr. |
| 3,895,405 A | 7/1975 | Edwards |
| 3,922,727 A | 12/1975 | Bianco |
| 3,975,350 A | 8/1976 | Hudgin et al. |
| 3,991,424 A | 11/1976 | Prahl |
| 4,010,052 A | 3/1977 | Edwards |
| 4,106,745 A | 8/1978 | Carrow |
| 4,133,776 A | 1/1979 | Pruett et al. |
| 4,282,325 A | 8/1981 | Rubenstein et al. |
| 4,283,800 A | 8/1981 | Wilson |
| 4,314,398 A | 2/1982 | Pettersson |
| 4,381,768 A | 5/1983 | Erichsen et al. |
| 4,404,296 A | 9/1983 | Schapel |
| 4,456,642 A | 6/1984 | Burgdorfer et al. |
| 4,466,936 A | 8/1984 | Schapel |
| 4,479,272 A | 10/1984 | Beldzisky |
| 4,623,354 A | 11/1986 | Childress et al. |
| 4,634,446 A | 1/1987 | Kristinsson |
| 4,635,626 A | 1/1987 | Lerman |
| 4,655,779 A | 4/1987 | Janowiak |
| 4,704,129 A | 11/1987 | Massey |
| 4,822,371 A | 4/1989 | Jolly et al. |
| 4,828,325 A | 5/1989 | Brooks |
| 4,888,829 A | 12/1989 | Kleinerman et al. |
| 4,908,037 A | 3/1990 | Ross |
| 4,923,475 A | 5/1990 | Gosthnian et al. |
| 5,007,937 A | 4/1991 | Fishman et al. |
| 5,108,455 A | 4/1992 | Telikicherla |
| 5,108,456 A | 4/1992 | Coonan, III |
| 5,133,776 A | 7/1992 | Crowder |
| 5,139,523 A | 8/1992 | Paton et al. |
| 5,163,965 A | 11/1992 | Rasmusson et al. |
| 5,201,774 A | 4/1993 | Greene |
| 5,211,667 A | 5/1993 | Danforth |
| 5,221,222 A | 6/1993 | Townes |
| 5,258,037 A | 11/1993 | Caspers |
| 5,314,497 A | 5/1994 | Fay et al. |
| 5,353,525 A | 10/1994 | Grim |
| 5,362,834 A | 11/1994 | Schapel et al. |
| 5,376,129 A | 12/1994 | Faulkner et al. |
| 5,376,131 A | 12/1994 | Lenze et al. |
| 5,376,132 A | 12/1994 | Caspers |
| 5,397,628 A | 3/1995 | Crawley et al. |
| 5,405,407 A | 4/1995 | Kodama et al. |
| 5,480,455 A | 1/1996 | Norvell |
| 5,490,537 A | 2/1996 | Hill |
| 5,507,834 A | 4/1996 | Laghi |
| 5,534,034 A | 7/1996 | Caspers |
| 5,549,709 A | 8/1996 | Caspers |
| 5,555,216 A | 9/1996 | Drouot |
| 5,571,208 A | 11/1996 | Caspers |
| 5,593,454 A | 1/1997 | Helmy |
| 5,658,353 A | 8/1997 | Layton |
| 5,658,354 A | 8/1997 | Norvell |
| 5,702,488 A | 12/1997 | Wood et al. |
| 5,702,489 A | 12/1997 | Slemker |
| 5,709,017 A | 1/1998 | Hill |
| 5,728,166 A | 3/1998 | Slemker |
| 5,728,167 A | 3/1998 | Lohmann |
| 5,728,168 A | 3/1998 | Laghi et al. |
| 5,728,169 A | 3/1998 | Norvell |
| 5,728,170 A | 3/1998 | Becker et al. |
| 5,732,578 A | 3/1998 | Kang |
| 5,735,906 A | 4/1998 | Caspers |
| 5,807,303 A | 9/1998 | Bays |
| 5,830,237 A | 11/1998 | Kania |
| 5,846,063 A | 12/1998 | Lakic |
| 5,888,216 A | 3/1999 | Haberman |
| 5,888,230 A | 3/1999 | Helmy |
| 5,888,231 A | 3/1999 | Sandvig et al. |
| 5,904,721 A | 5/1999 | Henry et al. |
| 5,904,722 A | 5/1999 | Caspers |
| 5,931,872 A | 8/1999 | Lohmann |
| 5,944,760 A | 8/1999 | Christensen |
| 5,980,577 A | 11/1999 | Radis et al. |
| 5,984,972 A | 11/1999 | Huston et al. |
| 6,007,582 A | 12/1999 | May |
| 6,063,125 A | 5/2000 | Arbogast et al. |
| 6,066,107 A | 5/2000 | Habermeyer |
| D429,335 S | 8/2000 | Caspers et al. |
| 6,117,117 A | 9/2000 | Mauch |
| 6,149,691 A | 11/2000 | Fay et al. |
| 6,231,616 B1 | 5/2001 | Helmy |
| 6,231,617 B1 | 5/2001 | Fay |
| 6,273,918 B1 | 8/2001 | Yuhasz et al. |
| 6,287,345 B1 | 9/2001 | Slemker et al. |
| 6,296,669 B1 | 10/2001 | Thorn et al. |
| 6,334,876 B1 | 1/2002 | Perkins |
| 6,361,568 B1 | 3/2002 | Hoerner |
| 6,362,387 B1 | 3/2002 | Carlson et al. |
| 6,402,788 B1 | 6/2002 | Wood et al. |
| 6,406,499 B1 | 6/2002 | Kania |
| 6,478,826 B1 | 11/2002 | Phillips et al. |
| 6,508,842 B1 | 1/2003 | Caspers |
| 6,544,292 B1 | 4/2003 | Laghi |
| 6,554,868 B1 | 4/2003 | Caspers |
| 6,589,289 B2 | 7/2003 | Ingimarsson |
| 6,602,295 B1 | 8/2003 | Doddroe et al. |
| 6,613,096 B1 | 9/2003 | Shirvis |
| 6,626,952 B2 | 9/2003 | Janusson et al. |
| 6,645,253 B2 | 11/2003 | Caspers |
| 6,673,117 B1 | 1/2004 | Soss et al. |
| 6,702,858 B2 | 3/2004 | Christensen |
| 6,706,364 B2 | 3/2004 | Janusson et al. |
| 6,726,726 B2 | 4/2004 | Caspers |
| 6,761,742 B2 | 7/2004 | Caspers |
| 6,767,370 B1 | 7/2004 | Mosler et al. |
| 6,797,008 B1 | 9/2004 | Arbogast et al. |
| 6,855,170 B2 | 2/2005 | Gramnas |
| 6,863,695 B2 | 3/2005 | Doddroe et al. |
| 6,926,742 B2 | 8/2005 | Caspers et al. |
| 6,964,688 B1 | 11/2005 | Kania |
| 6,969,408 B2 | 11/2005 | Lecomte et al. |
| 6,974,484 B2 | 12/2005 | Caspers |
| 7,025,792 B2 | 4/2006 | Collier |
| 7,025,793 B2 | 4/2006 | Egilsson |
| 7,371,262 B2 | 5/2008 | Lecomte et al. |
| 7,427,297 B2 | 9/2008 | Patterson et al. |
| 7,448,407 B2 | 11/2008 | Alley et al. |
| 7,468,079 B2 | 12/2008 | Collier |
| 7,686,848 B2 | 3/2010 | Christensen |
| 7,744,653 B2 | 6/2010 | Rush et al. |
| 7,909,884 B2 | 3/2011 | Egilsson et al. |
| 7,922,775 B2 | 4/2011 | Caspers |
| 7,947,085 B2 | 5/2011 | Haines et al. |
| 7,993,413 B2 | 8/2011 | Perkins et al. |
| 8,007,543 B2 | 8/2011 | Martin |
| 8,034,120 B2 | 10/2011 | Egilsson et al. |
| 8,052,760 B2 | 11/2011 | Egilsson et al. |
| 8,097,043 B2 | 1/2012 | Egilsson |
| 8,097,766 B2 | 1/2012 | Carlson et al. |
| 8,114,167 B2 | 2/2012 | Caspers |
| 8,298,294 B2 | 10/2012 | Kaltenborn et al. |
| 8,317,876 B2 | 11/2012 | Mosler |
| 8,343,233 B2 | 1/2013 | Perkins et al. |
| 8,523,951 B2 | 9/2013 | Kania |
| 8,956,422 B2 | 2/2015 | Halldorsson |
| 8,961,618 B2 | 2/2015 | Lecomte et al. |

(56) References Cited

U.S. PATENT DOCUMENTS

| | | |
|---|---|---|
| 9,066,822 B2 | 6/2015 | Caldwell et al. |
| 2001/0005798 A1 | 6/2001 | Caspers |
| 2001/0016781 A1 | 8/2001 | Caspers |
| 2002/0087215 A1 | 7/2002 | Caspers |
| 2002/0091449 A1 | 7/2002 | Caspers et al. |
| 2002/0103545 A1 | 8/2002 | Arbogast et al. |
| 2002/0128580 A1 | 9/2002 | Carlson et al. |
| 2003/0191539 A1 | 10/2003 | Caspers |
| 2004/0024322 A1 | 2/2004 | Caspers |
| 2004/0064195 A1 | 4/2004 | Herr |
| 2004/0122528 A1 | 6/2004 | Egilsson |
| 2004/0163278 A1 | 8/2004 | Caspers et al. |
| 2004/0181290 A1 | 9/2004 | Caspers |
| 2004/0236434 A1 | 11/2004 | Carstens |
| 2004/0260403 A1 | 12/2004 | Patterson et al. |
| 2005/0131549 A1 | 6/2005 | Caspers |
| 2005/0143838 A1 | 6/2005 | Collier |
| 2005/0240282 A1 | 10/2005 | Rush et al. |
| 2006/0212130 A1 | 9/2006 | Collier |
| 2006/0212131 A1 | 9/2006 | Curtis |
| 2007/0005149 A1 | 1/2007 | Egilsson et al. |
| 2007/0043316 A1 | 2/2007 | Carlson et al. |
| 2007/0055383 A1 | 3/2007 | King |
| 2007/0112440 A1 | 5/2007 | Perkins et al. |
| 2007/0196222 A1 | 8/2007 | Mosler et al. |
| 2008/0086218 A1 | 4/2008 | Egilsson |
| 2008/0269911 A1 | 10/2008 | Street et al. |
| 2008/0269912 A1 | 10/2008 | Gobbers et al. |
| 2009/0036998 A1 | 2/2009 | Finlinson et al. |
| 2009/0132056 A1 | 5/2009 | Kania |
| 2009/0157196 A1 | 6/2009 | Danzig et al. |
| 2009/0198346 A1 | 8/2009 | Perkins et al. |
| 2009/0204229 A1 | 8/2009 | Mosler et al. |
| 2010/0070051 A1 | 3/2010 | Carstens |
| 2010/0087931 A1 | 4/2010 | Bogue |
| 2010/0106260 A1 | 4/2010 | Phillips |
| 2010/0262261 A1 | 10/2010 | Laghi |
| 2010/0312359 A1 | 12/2010 | Caspers |
| 2010/0312360 A1 | 12/2010 | Caspers |
| 2011/0035027 A1 | 2/2011 | McCarthy |
| 2011/0071649 A1 | 3/2011 | McKinney |
| 2011/0130846 A1 | 6/2011 | Kampas et al. |
| 2011/0202143 A1 | 8/2011 | Caspers |
| 2011/0295386 A1 | 12/2011 | Perkins et al. |
| 2012/0123559 A1 | 5/2012 | Mosler et al. |
| 2012/0173000 A1 | 7/2012 | Caspers |
| 2012/0173001 A1 | 7/2012 | Caspers |
| 2012/0191217 A1 | 7/2012 | Mackenzie |
| 2013/0053982 A1 | 2/2013 | Halldorsson |
| 2013/0096694 A1* | 4/2013 | Caldwell et al. ............ 623/34 |
| 2013/0211544 A1 | 8/2013 | Jonsson et al. |
| 2013/0282142 A1 | 10/2013 | Perkins et al. |
| 2013/0289741 A1 | 10/2013 | Halldorsson et al. |

FOREIGN PATENT DOCUMENTS

| | | |
|---|---|---|
| CA | 2098945 C | 7/1997 |
| CN | 101815870 A | 8/2010 |
| DE | 685 861 C | 12/1939 |
| DE | 745981 C | 5/1944 |
| DE | 2712342 A1 | 9/1977 |
| DE | 2729800 A1 | 1/1979 |
| DE | 3221920 A1 | 4/1983 |
| DE | 4217877 A1 | 12/1992 |
| DE | 4321182 C1 | 12/1994 |
| DE | 9418210 U1 | 1/1995 |
| DE | 9419211 U1 | 2/1995 |
| DE | 9417913 U1 | 3/1995 |
| DE | 29905020 U1 | 7/1999 |
| EP | 0019612 A1 | 11/1980 |
| EP | 0057838 A1 | 8/1982 |
| EP | 0057839 A1 | 8/1982 |
| EP | 0086147 A1 | 8/1983 |
| EP | 0261884 A1 | 3/1988 |
| EP | 0320170 A1 | 6/1989 |
| EP | 0363654 A2 | 4/1990 |
| EP | 0631765 A1 | 1/1995 |
| EP | 0650708 A1 | 5/1995 |
| EP | 0870485 A2 | 10/1998 |
| EP | 1509176 A1 | 3/2005 |
| EP | 1875881 A1 | 1/2008 |
| FR | 1135516 A | 4/1957 |
| FR | 1532625 A | 7/1968 |
| FR | 2420035 A1 | 10/1979 |
| FR | 2501999 A1 | 9/1982 |
| GB | 136504 A | 12/1919 |
| GB | 267988 A | 3/1927 |
| GB | 2069847 A | 9/1981 |
| GB | 2149309 A | 6/1985 |
| JP | 7155343 A | 6/1995 |
| RU | 1771722 A1 | 10/1992 |
| RU | 1812982 A3 | 4/1993 |
| RU | 1821177 A1 | 6/1993 |
| SE | 8801686 L | 3/1989 |
| SU | 1667855 A1 | 8/1991 |
| WO | 8400881 A1 | 3/1984 |
| WO | 9505792 A1 | 3/1995 |
| WO | 9621405 A1 | 7/1996 |
| WO | 9804218 A1 | 2/1998 |
| WO | 9855055 A1 | 12/1998 |
| WO | 9905991 A2 | 2/1999 |
| WO | 9965434 A1 | 12/1999 |
| WO | 0003665 A1 | 1/2000 |
| WO | 0074611 A2 | 12/2000 |
| WO | 0154631 A1 | 8/2001 |
| WO | 0170147 A2 | 9/2001 |
| WO | 0226158 A2 | 4/2002 |
| WO | 02065958 A2 | 8/2002 |
| WO | 02067825 A2 | 9/2002 |
| WO | 02080813 A2 | 10/2002 |
| WO | 03077797 A2 | 9/2003 |
| WO | 03099173 A1 | 12/2003 |
| WO | 03099188 A1 | 12/2003 |
| WO | 2005039444 A2 | 5/2005 |
| WO | 2005105000 A1 | 11/2005 |
| WO | 2006/012820 A1 | 2/2006 |
| WO | 2010141960 A2 | 12/2010 |
| WO | 2011035099 A1 | 3/2011 |
| WO | 2012/177965 A1 | 12/2012 |

OTHER PUBLICATIONS

Brochure, "Sometimes Less is More, Harmony P3" Otto Bock, 12 pages. Available at, http://www.ottobock.com/cps/rde/xbcr/ob_es/646A303-EN-01-1001w.pdf, dated 2012.

Information Guide, "Harmony Users Guide Otto Bock, 9 pages, available at http://media.ottobock.com/Prosthetics/Socket-Technologies/Harmony/_Genreal/Files/12072403.1_OB-Harmony-UsersGuide-9-10-12.pdr", dated 2012.

Brochure, "Harmony Certification Course Manual, Original Harmony Pump, 42 pages. Availiable at, http://academy.ottobockus.com/videos/harmony/data/downloads/harmony%20course%20manual%202013.pdf." Dated 2013.

Brochure, Harmony P2 & HD, 2 pages. Available at http://www.ottobock.com/cps/rde/xchg/ob_us_en/hs.xsl/14904.html?id=4641. Dated 2012.

International Search Report from corresponding PCT Application No. PCT/US2013/025849, Jun. 4, 2013.

International Search Report and Written Opinion Regarding Application No. PCT/US2013/038668, Aug. 7, 2013.

Haberman, Louis J., "Silicone-Only Suspension (SOS) with Socket-Loc and the Ring for the Lower Limb", found at, http://www.oandp.org/jpo/library/1995_01_002.asp. Journal of Prosthetics and Orthotics 1995; vol. 7, No. 1, p. 2, 19 pages, dated 2012.

Chinese Examination Report from Chinese Application No. 201380022874.0, Aug. 25, 2015.

International Search Report from corresponding International PCT Application No. PCT/US2015/037204, Sep. 25, 2015.

* cited by examiner

VACUUM SUSPENSION SYSTEM

TECHNICAL FIELD

The present disclosure relates to an improved vacuum suspension system for securing a prosthetic socket to a user.

BACKGROUND

Amputees commonly use prosthetic devices to improve their mobility and associated quality of life. Various types of prostheses exist for replacing the functionality of a missing limb. Transtibial and transfemoral prostheses are effective at helping amputees regain the ability to walk on their own. Various forces cause separation between a prosthetic limb and a residual limb, especially during use. This may happen during the swing phase of ambulation, when a prosthetic leg is subjected to both gravitational and centrifugal forces.

The manner in which an artificial limb is attached to a residual limb determines the control an amputee has over the prosthesis. Traditionally, prostheses are secured to amputees' residual limbs by straps, belts, cuffs, harnesses and/or locking pins. These devices are inconvenient and uncomfortable. They cause chafing against the patient's body, which leads to sores and abrasions. It is now common to use some type of suspension system.

Amputees can secure prosthetic devices on their residual limbs by using various vacuum or suction arrangements, whereby the maximum strength of the force holding the prosthesis to the residual limb is a function of the atmospheric pressure. The differential air pressure is routinely referred to as suction or vacuum by those having skill in the art. To maintain the sub-atmospheric pressure created within the distal end of the socket, sealing sleeves or liners have been provided to prevent an influx of air around the distal end of the residual limb. Such liners are provided between the residual limb and the socket to provide for slight compression, and a gripping connection is provided to assist with the suction suspension.

The liner can be rolled onto the residual limb so the liner-covered limb can then be inserted into the prosthetic socket. The use of conventional liners alone only provides a partial suction fit since they do not form a true air-tight seal with the socket. Some air will slowly enter the socket, especially during the swing phase of the patient's gait and during periods of inactivity.

Conventional vacuum systems have been used to increase the suction within the socket. Such vacuum systems may utilize a valve at a distal end of an otherwise closed socket arranged to receive the distal end portion of a residual limb. These pressure-control systems work by exhausting air only from the space between the distal end of the residual limb and the distal end of the socket interior as the limb is fully inserted into the socket. Any air that has migrated to areas other than the distal end can remain trapped, and this action affects the optimal pressure differential and diminishes the strength of the suction connection. There is a clear need to provide a way to allow a user to expel air from within any area of the socket.

The use of a valve is intended to allow air to be expelled from the socket in order to maintain at least a slight negative pressure for creating suction against the residual limb. Although the swing phase of the gait cycle will tend to pull the socket off the limb, walking and other weight-bearing activities may push the limb further into the socket. Pushing the limb further into the socket causes the valve to expel air. Conversely, directly pulling the limb out of the socket is prohibited due to the effect of suction.

Common valve systems used with prosthetic sockets have included an inner base connected to an outer housing that can be threaded directly to the socket wall. These types of valve systems often fail at maintaining the desired air pressure within the socket because they are installed on flat socket wall surfaces. The inclusion of a threaded outer housing helps to prevent air from leaking out of the socket from around the housing instead of being expelled through the valve as intended. Without an air-tight seal in a vacuum suspension system, any significant loss of suction will cause separation of the prosthesis from the residual limb. Thus there is a clear need to provide a valve arranged in a suspension system that can be adapted for effective use on a curved portion of a socket wall surface.

Other traditional sockets may include a separate, self-contained vacuum reservoir for maintaining the sub-atmospheric pressure within the socket interior. However, the vacuum systems create additional bulk and add weight to the socket, making it more difficult for an amputee to achieve natural mobility with the attached prosthetic. Attaching such a reservoir may also decrease the structural integrity of the socket since it may no longer conform to the residual limb and provide a smooth and comfortable fit if it collapses.

It has been found that total contact between a residual limb and a prosthetic socket is important to attain an even weight distribution of the patient, which helps distribute the suspension of the prosthesis over the whole surface of the limb. As the wearer sweats, losing fluid causes the volume of the residual limb to decrease, which correspondingly alters the fit of the residual limb within the socket. Therefore, there is also a need to improve the consistency and reliability of the fit between the residual limb and the socket.

Many existing valve systems include components protruding from the socket, making it cumbersome and uncomfortable to wear, while also increasing the chance it may snag onto foreign objects. By not keeping a low profile, there is also a greater likelihood of the valve system being damaged. Damaging the valve would cause the air pressure within the socket to no longer be properly maintained, and the vacuum suspension it provides to the residual limb would ultimately fail. There is a clear need for an improved pressure regulation system that is not burdensome or uncomfortable for a user, and which maintains a low profile.

Using a conventional valve system alone may not be an effective or efficient way to expel excess air from within the socket. Instead, it is a goal behind embodiments of the disclosure to provide a valve system with an improved pump to create the desired vacuum effect. Including such a pump would ensure a sufficient amount of air is expelled from the socket to create the desired suction.

Current pumps used with prosthetic sockets have disadvantages, including their size, weight and difficulty of use. For many patients, the time-consuming steps involved with operating the pump combined with the cumbersome placement and unreliability of accurately regulating pressure convinces them to avoid using prostheses entirely. There is therefore a need to provide an easy and quick way of adjusting the fit of the residual limb within the socket, while making the prosthesis easier to don and doff without sacrificing comfort.

It can be seen from the foregoing there are many needs for improving on the drawbacks of conventional vacuum suspension systems for attaching to prosthetic sockets. The embodiments of the present disclosure address these aforementioned shortcomings of known prosthetic systems.

SUMMARY

According to various embodiments, a vacuum suspension system is provided for securing an amputee's residual limb to a prosthetic device. Placing a vacuum pump directly on a socket according to the present disclosure provides a slim and effective way to ensure there is sufficient suction suspension to maintain a residual limb engaged with a prosthetic socket. The differential air pressure caused by using a vacuum pump creates suction that helps retain or suspend a residual limb to and within a prosthetic socket.

It should be appreciated that a liner may be worn over the residual limb so it is positioned within the hard socket to ensure the suction suspension created by the vacuum pump works as intended. Using a liner to provide a tight fit for the residual limb within a socket also helps prevent air from entering the socket interior from outside of the socket. Using vacuum pressure to maintain a reliable connection with a residual limb improves the fit and comfort between the socket and limb. As noted, air can enter the socket interior during use if the liner does not form a strong air-tight seal with the socket.

It is a goal behind embodiments of the disclosure to use a vacuum pump to expel air from a region between the socket interior and the liner-sheathed residual limb. The presence of extraneous air within the socket decreases the suction applied to the residual limb, which may cause it to become disengaged from the socket during use. It is desired to increase the negative pressure within this region as air is drawn out, thereby increasing the suction available to hold the prosthesis to the residual limb. The more suction used, however, may amplify any patient discomfort.

It is another goal of the present disclosure to provide a vacuum source that a patient can control as desired to prevent possible chafing of the residual limb. Further, it is advantageous to have a suction suspension system that a patient can adjust so that wearing a prosthetic device is comfortable. A valve system in combination with a vacuum pump is an effective way to regulate a comfortable, yet effective level of suction suspension.

Yet another goal of the embodiments of the present disclosure offers a fast and efficient way to operate a vacuum pump. It is advantageous to provide an amputee with an easy and reliable way of connecting the vacuum pump on the socket. The vacuum pump of various embodiments offers a practical solution for an amputee who would otherwise need to carry around a portable a vacuum and regularly adjust the level of suction suspension when needed. By attaching the vacuum pump directly to the socket as in the embodiments, less risk of breakage can result from repeatedly re-attaching an external vacuum source.

The embodiments of the vacuum suspension system of the present disclosure provide a quick, easy and reliable way to regulate the level of suction suspension in a prosthetic socket. By providing a hand-operated pump secured directly on the socket, a patient can adjust the desired level of suction suspension on the fly during use or when initially donning the prosthesis. It should be appreciated the vacuum pump of various embodiments is relatively unobtrusive when positioned on a socket. This allows the prosthesis as a whole to keep a low profile so a user does not have to worry about constantly bumping or snagging the pump on foreign objects.

In an embodiment, a vacuum suspension system includes a rigid socket defining a socket wall having exterior and interior surfaces. The socket defines an aperture extending between the exterior and interior surfaces and has a closed distal end and an open proximal end with the socket forming an interior cavity defined by the interior surface. A fluid regulator, such as a one-way valve, is provided at the aperture. The socket is preferably sealed at the proximal end and is generally impermeable to air. Various means may be employed to seal the proximal end of the socket, including a sealing sleeve or rolling a portion of a liner over the brim of the socket.

A pump system includes a pump and a covering for securing over the exterior surface of the socket and carrying the pump. The pump is configured for placement proximate to the fluid regulator and arranged for drawing air from the socket through the aperture and operatively engaging the fluid regulator. A chamber having a variable volume is formed by a space defined between the exterior surface and an inner surface of the covering proximate to the pump.

The pump system may include activation means for expanding and decreasing the volume of the chamber. For example the activation means include a handle arranged for operating the fluid regulator and drawing air from the socket cavity. In a variation, the the handle is generally elastic and returns to a predetermined first position both prior to and at release thereof, as the handle is pulled away from the exterior surface of the socket.

The covering may be arranged to seal against the exterior surface of the socket and selectively prevent escape of air from an interface formed between the covering and the exterior surface. In a variation, the covering is air impermeable and seals against the exterior surface of the socket by compression of the covering against the socket. The covering may be arranged to permit escape of air from the chamber upon release of a handle belonging to a variation of the pump system, and forms a one-way valve with the exterior surface of the socket. The covering may have a channel permitting air to escape from the chamber.

The covering may be air impermeable and elastic, and may be substantially more flexible than the exterior surface of the socket.

Various types of pumps are disclosed and arranged to operatively expand the chamber and draw air from the socket through the fluid regulator. The covering may be adapted in a variety of configurations to permit escape of air from the chamber after or during withdrawal of air from the socket.

These and other features, aspects, and advantages of the present disclosure will become better understood regarding the following description, appended claims, and accompanying drawings.

BRIEF DESCRIPTION OF THE DRAWINGS

FIG. 12(*c*) is a top plan view of the on-socket vacuum pump according to FIGS. 12(*a*) and 12(*b*).

Figure 1:
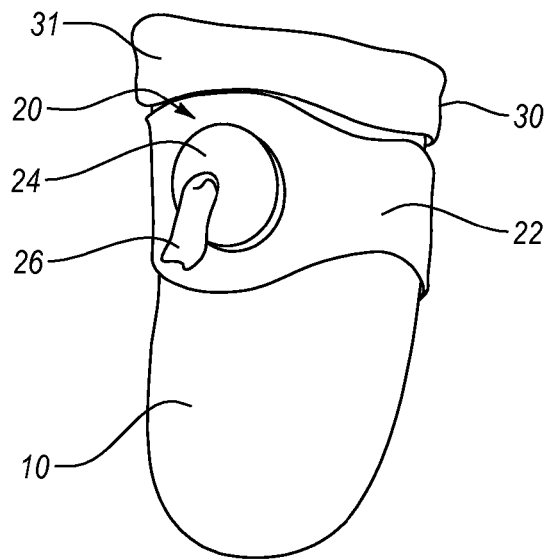
FIG. 1 is a perspective view of a vacuum suspension system secured to a prosthetic socket according to an embodiment of the disclosure.

The drawing figures are not drawn to scale, but instead are drawn to provide a better understanding of the components, and are not intended to be limiting in scope, but rather to provide exemplary illustrations. The figures illustrate exemplary embodiments of a vacuum suspension system and the components, and in no way limit the structures or configurations of a vacuum suspension system and components according to the present disclosure.

DETAILED DESCRIPTION OF VARIOUS EMBODIMENTS

A. Overview

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that, unless a term is expressly defined in this disclosure to possess a described meaning, there is no intent to limit the meaning of such term, either expressly or indirectly, beyond its plain or ordinary meaning.

The vacuum suspension system described is configured for use with a prosthetic socket, such as a lower leg prosthesis. It should be remembered, however, that the same concepts and methods described may be similarly used for other prosthetic devices and are not limited solely to the anatomical locations discussed.

General anatomical terms for the human body may be used for describing particular locations of the elements of the vacuum suspension system in comparison to the human body.

The terms "proximal" and "distal" generally refer to areas on the prosthetic socket that correspond to a location relative to where a residual limb can be inserted. For instance, the proximal end of the socket is its open end where a residual limb is first inserted into. The distal end of the socket is opposite the proximal end and includes at least part of a cavity of the socket arranged to receive a residual limb.

B. Environment and Context of the Various Embodiments

The vacuum suspension system of the present disclosure is described for use with a hard unitary prosthetic socket. This socket defines a shell having a receiving portion for a residual limb and an interior chamber for accommodating the residual limb. The shell is preferably structurally rigid and air impervious. It should be appreciated that many configurations of the socket shell may be used with the vacuum suspension system.

Various embodiments of the vacuum suspension system may be incorporated into many prosthetic appliances, including above and below the knee lower limb prosthetics, and upper limb prosthetics. While the advantages of the vacuum suspension system are discussed with respect to lower limb prostheses, similar advantages can be achieved when the vacuum suspension system applies to upper limb prostheses.

The prosthetic socket of the present disclosure relies on vacuum pressure to ensure a secure connection with a residual limb, while also improving the fit and comfort between the socket and limb. The differential air pressure caused by using a vacuum pump creates a suction effect that helps retain or suspend a residual limb within a prosthetic socket.

To ensure that the suction suspension created by the vacuum pump works as intended, a liner may be worn over the residual limb so it is positioned within the hard socket. Besides assisting with suction inside the socket so the residual limb does not fall out, a liner may also be worn to provide cushioning to the limb and to provide a gripping connection to the interior surface of the socket. Using a liner to provide a tight fit for the residual limb within a socket also helps prevent air from entering the socket interior from outside of the socket.

An example of a socket and method for making the same are found in U.S. Pat. No. 5,885,509, granted Mar. 23, 1999, and U.S. Pat. No. 7,105,122, granted Sep. 12, 2006, both incorporated herein by reference. An exemplary liner sleeve for combination with the socket is found in U.S. Pat. No. 6,136,039, granted Oct. 24, 2000, U.S. Pat. No. 6,626,952, granted Sep. 30, 2003, U.S. Pat. No. 6,485,776, granted Nov. 26, 2002, U.S. Pat. No. 6,706,364, granted Mar. 16, 2004, U.S. Pat. No. 7,001,563, granted Feb. 21, 2006, and U.S. Pat. No. 7,118,602, granted Oct. 10, 2006, each of which are incorporated herein by reference in their entirety.

If the liner may not provide a true air-tight seal with the socket, some air will slowly enter the socket interior during use. The presence of additional air within the socket would disrupt the pressure differential between the inside of the socket and the surrounding ambient air outside the socket, thus decreasing the suction and potentially causing the limb to become disengaged from the socket.

It is important to provide a sufficient amount of suction for suspending a prosthesis to a residual limb during ambulation. Air may be drawn into the interior of conventional sockets during the repeating phases of a normal gait cycle. The repetitive motions displayed between the stance and swing phases of walking generate a pumping and pistoning effect within the socket, which draws in air. Even conventional prosthetic sockets with sealing systems sometimes experience some air leaking into the socket interior over a course of use.

When the pressure within the socket reaches atmospheric pressure, the increased volume of air inside will allow the residual limb to move within the socket and potentially separate altogether. Any extraneous movement of the limb within the socket could cause the patient additional medical problems, including chafing of the skin. Moreover, patients who notice a loose connection between the residual limb and the prosthesis may also suffer increased anxiety stemming from their insecurity regarding whether and/or when the prosthesis will fall off their limb.

To combat this problem, the vacuum suspension system of the present disclosure can include an on-socket vacuum pump to expel air from the region between the socket interior and the liner-sheathed residual limb. The negative pressure within this space increases as air is drawn out, correspondingly increasing the suction available to hold the prosthesis to the residual limb.

A greater amount of suction results in a more secure connection between the socket and the limb. The more suction used may correlate to an increase in patient discomfort since more chafing and/or compression may be felt, which could further affect blood flow and circulation within the limb.

Including a valve system in combination with the vacuum pump can help regulate a comfortable, yet effective pressure differential within the socket for maintaining an appropriate level of suction suspension. Using a valve system is also helpful in preventing a positive pressure within the socket interior relative to the ambient air outside the socket to allow donning the prosthesis on a limb. When used in combination with the aforementioned vacuum pump, a valve system utilizing a check valve can provide partial suction created naturally during ambulation. For instance, walking promotes weight-bearing of the limb within the socket during the stance phase. This expels air from the socket maintaining a slight negative pressure inside the socket relative to the ambient pressure outside.

Using a vacuum pump system by itself can therefore provide a desired amount of suction within a socket including during ambulation or while motionless. Alternatively, it can supplement the amount of suction produced by a valve during ambulation or when the socket is initially donned. Conventional vacuum systems, however, are bulky and often difficult to operate. This is because they must be connected to an external vacuum source provided separately from the prosthesis.

Properly connecting the vacuum pump to a prosthesis can be a very time-consuming process, and may not be very reliable since such vacuum pumps will not work to create an adequate amount of suction within the socket if they are not correctly attached. This makes it risky for an amputee to depend on such vacuum pumps for maintaining adequate suction within a socket. This applies especially to electric pumps, which have the tendency to break down and need repairs. It can also be impractical for a patient to carry around such a vacuum source over a day since it can be rather heavy. There is a greater chance that having to frequently attach and detach a vacuum source can cause it to break or become damaged due to extended wear and tear.

Embodiments of the vacuum suspension system of the present disclosure provide a quick, easy and reliable way to regulate the air differential within a prosthetic socket for adjusting the level of suction. By providing a hand-operated pump secured directly on the socket, a patient can adjust the desired level of suction suspension on the fly during use or when immobile, such as when initially donning the prosthesis. Another advantage of the vacuum suspension system of the present disclosure is that the on-socket vacuum pump is very slim, which allows the prosthesis as a whole to keep a low profile so a user does not have to worry about constantly bumping or snagging the pump on foreign objects. It can be attached to most existing prosthetic sockets since it is both easy to use and to install. It should also be appreciated that placing the vacuum pump on the socket helps preserve the socket's structural integrity since only a small hole must be created on the socket for the pump to work as intended.

C. Embodiments of the Vacuum Suspension System

Under a first embodiment of the disclosure illustrated in FIGS. 1-4, the vacuum suspension system 20 is arranged on a hard prosthetic socket 10. An on-socket vacuum pump 24 is shown partially formed by the exterior surface of the socket 10 in combination with a retaining covering 22 that slides over the exterior surface of the socket. It is advantageous that the covering 22 is both elastic and removably attachable to the socket 10 so that a patient can easily clean the socket and other component parts of the prosthesis and/or pump. This also allows the individual parts to be easily replaced or repaired if they become damaged.

The covering 22 is preferably fabricated from an impermeable material. Making the pump 24 detachable by sliding the covering 22 off the socket 10 allows a user to remove the pump in situations that otherwise might cause damage without compromising the suction suspension within the socket.

A variety of suitable synthetic materials that are fluid tight, including several different plastics and/or resins, may produce the socket 10. The socket is preferably rigid and can be formed by lamination or fabricated using various copolymers such as polyethylene or polypropylene. Further, the socket may be fabricated based on patient-specific anatomy and volume.

The socket 10 is donned over the patient's residual limb. A soft gel-like interface liner 30 is placed on the residual limb before the limb is inserted into the socket 10. Similar to the covering 22, the socket liner 30 is preferably fabricated from silicone or other impermeable material. Because of the gel-like qualities of the liner, it may need to be rolled onto the limb rather than directly pulled on like a sock. Rolling the liner 30 on the limb in this fashion ensures there is only a miniscule amount of air remaining between the limb and the inner surface of the liner. The liner 30 is intended to provide a snug fit against the entire circumference of the limb. Providing a tight fit helps stop air from entering the space between the liner and the limb. This type of fit is also important to prevent the liner from being loosened or removed from the limb when tension is applied.

The liner 30 may also provide additional cushioning to the residual limb. The liner may create an air-tight seal for trapping air within the space between the socket interior and the exterior of the liner. This is accomplished by folding a proximal end 31 of the liner 30 over the outer rim 12 of the socket at its proximal end as shown in FIG. 1. Preferably the prosthetic socket 10 is rigid so the seal formed with the liner 30 is air tight. Partial suction may form between the liner-sheathed limb and the socket. Maintaining such partial suction is possible if the liner is properly contoured to the shape of the residual limb. It is preferable there are no un-sealed holes in the socket that could allow air to enter.

A total suction fit between the liner-sheathed limb and the socket, however, requires using the on-socket vacuum pump 24. A vacuum for expelling excess air from within the socket interior may be used if the sealing engagement fails between the liner 30 and the outer rim 12 of the socket on which the liner is rolled over. In this situation, a slow air leak at this seal would increase the air pressure within the socket, and correspondingly cause a slow decrease for suction suspension provided by the socket.

The vacuum pump 24 may have the shape of a dome and may be integrally formed on the covering 22. The covering 22 may be formed as a sleeve with open proximal and distal ends.

Figure 2:
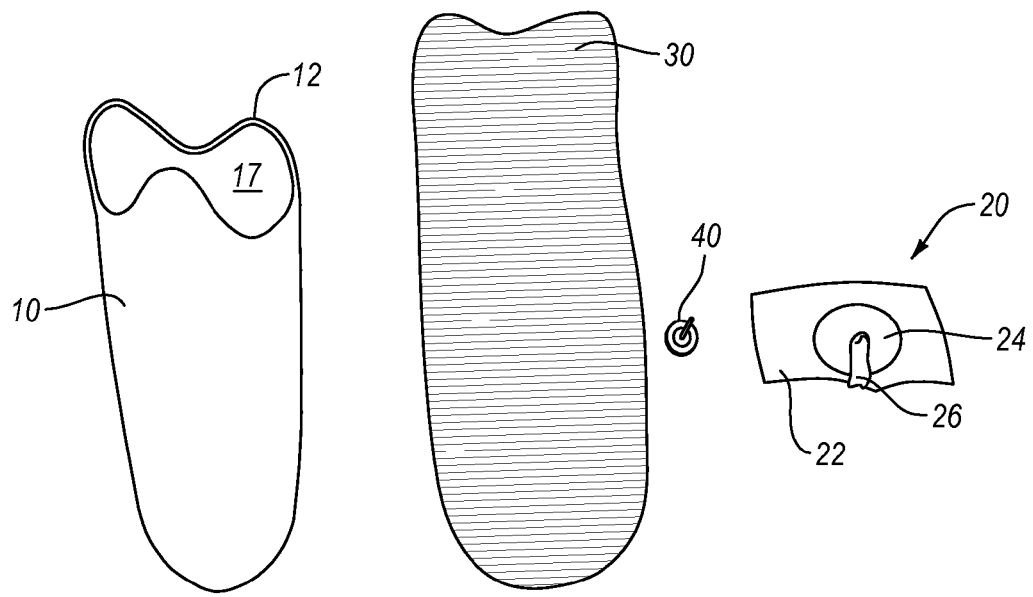
FIG. 2 is a front elevational view illustrating each individual component of the on-socket vacuum pump assembly according to the embodiment of FIG. 1.
Figure 3:
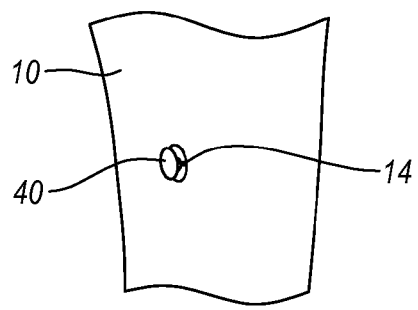
FIG. 3 is a schematic view of the prosthetic socket of FIG. 1 with a valve attached thereto.
Figure 4:
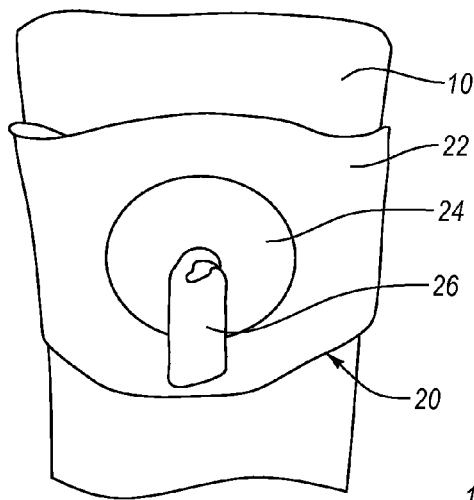
FIG. 4 is a front elevation view of the embodiment of FIG. 1 without the liner.

The covering 22 is slipped over a exterior surface 13 of the socket such that the vacuum pump 24 is positioned over a hole 14 on the socket wall as shown in FIGS. 2-4. The hole 14 extends between the exterior surface 13 of a socket wall 11 to and interior surface 15 of the socket wall 11. The interior surface 15 defines an interior cavity 17, as the socket has a closed distal end and an open proximal end.

A fluid regulator 40 is preferably situated within the hole 14 on the socket 10 to control fluid flow between the interior and exterior of the socket. Preferably, the fluid regulator may be a valve, and should regulate the air pressure within the socket so an undesirable pressure differential does not adversely affect donning and doffing.

The valve helps maintain a sufficient amount of suction suspension for the prosthesis and regulates the air pressure in the socket so undesirable pressure differentials do not prevent or complicate the donning and doffing of the socket. Valves should relieve buildup of pressure when the liner-sheathed residual limb is inserted into the socket. This aids in preventing a positive internal pressure relative to the ambient air outside of the socket to allow for donning.

The valve 40 preferably may be a one-way valve, also referred to as a check valve. A preferred type of one-way valve used with the vacuum pump is a mushroom valve. It should be appreciated, however, that other types of one-way valves may be described herein. The one-way valve only allows air to be expelled from the socket for maintaining an internal negative air pressure relative to the ambient air pressure outside the socket assisting in sustaining suction. The valve must be maintained in a closed position so the induced sub-atmospheric pressure between the distal end of the residual limb and distal end of the prosthetic socket resists the forces separating the socket from the limb.

The valve 40 is shown located within the wall of the socket 10 in FIG. 3, but may also be located near other areas on the socket as desired if the valve remains in fluid communication with an interior portion of the socket where the patient's residual limb resides. This is suitable if negative air pressure is formed when the residual limb is pushed deep into the socket, expelling any remaining air. Placing the valve in the intermediate section or upper section is preferable to allow the user to more easily reach the pump 24, and avoids potential interference with a prosthesis attached to the distal end 31 of socket.

In order to easily and quickly create sufficient suction suspension, the vacuum pump 24 can allow a user to remove any extra air left inside of the socket 10 that the valve 40 may fail to expel when the socket is first donned. Creating a stronger suction suspension than what was initially obtained is useful to expel additional air out from the socket before the user even takes a first step. By manually activating the vacuum pump 24 repeatedly to expel air from the socket interior, the vacuum suspension system 20 offers an amputee superior control over the level of suction suspension desired.

Using the on-socket vacuum pump 24 as discussed allows the patient to determine the strongest suction suspension desired while still remaining comfortable. Aligning the vacuum pump 24 directly over the valve 40 allows the user to pump air out of the socket interior. This can be accomplished by manually operating the pump by hand. The pump 24 may include a handle 26 attached thereto, such that when the handle is pulled, the internal vacuum releases the valve from the socket wall and draws air out of the socket 10. The vacuum pump 24 forces air out of the socket 10 through the one-way valve 40 with every pull, consequently increasing the negative pressure within the socket.

The section of the covering 22 integrally formed with the pump 24 is preferably sealed against the exterior surface of the socket to maintain the resulting vacuum pressure created from pulling the handle 26. This sealing force is caused by the compression provided by the covering 22 against the socket 10. Since the socket 10 is hard, the seal formed with the covering 22 is air-tight.

Figure 5A:
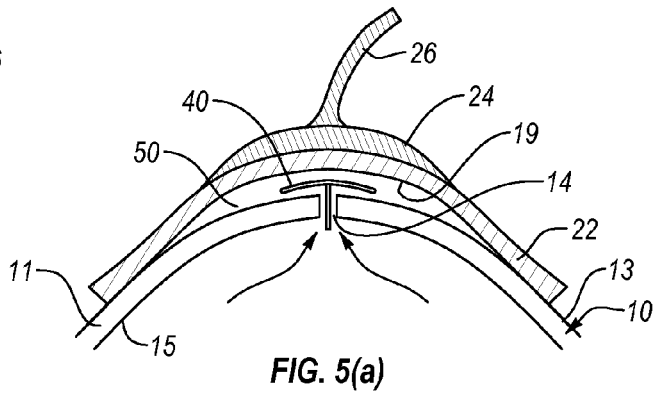
FIGS. 5(a)-5(c) are cross-sectional views showing how the on-socket vacuum pump of FIG. 4 is operated.

As illustrated in FIG. 5(a), when the handle 26 is first pulled, air within the socket interior may evacuate from the socket interior through the valve 40. The air expelled from the socket interior by the pump is collected in a chamber 50 having a variable volume defined by the space created between the exterior of the socket and an inner surface 19 of the covering adjacent to the location where the pump is located.

Figure 5B:
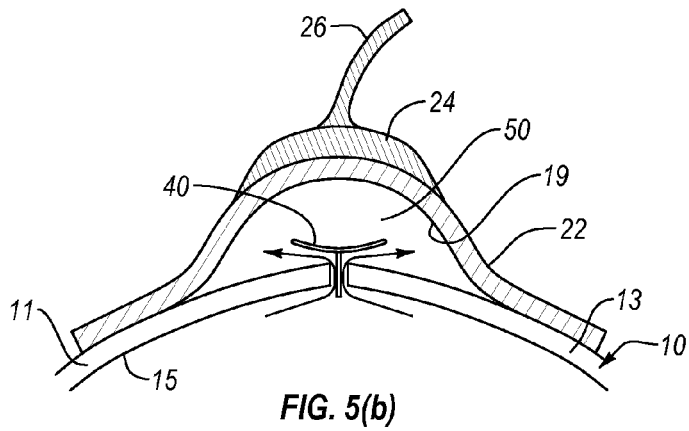
Figure 5C:
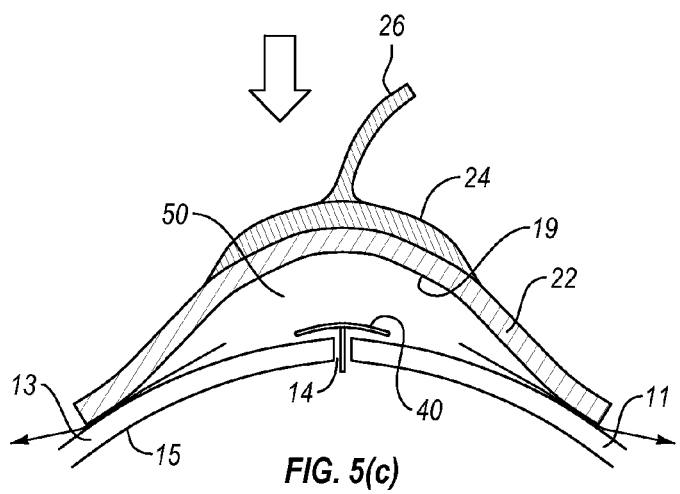

Turning to FIG. 5(b), the chamber 50 expands to hold more air coming through the valve 40 from the socket interior as the handle 26 is pulled. Upon releasing the pump handle 26, the air collected in the chamber 50 is subsequently expelled to the atmosphere from under the peripheral ends of the covering 22. A portion of the covering 22 may function as a second fluid regulator, such as a one-way valve, to let air out of the chamber 50 along the exterior surface of the socket. Manually pumping out more air from the socket not only improves suspension, but offers better control and less pressure on the limb and liner.

Figure 6:
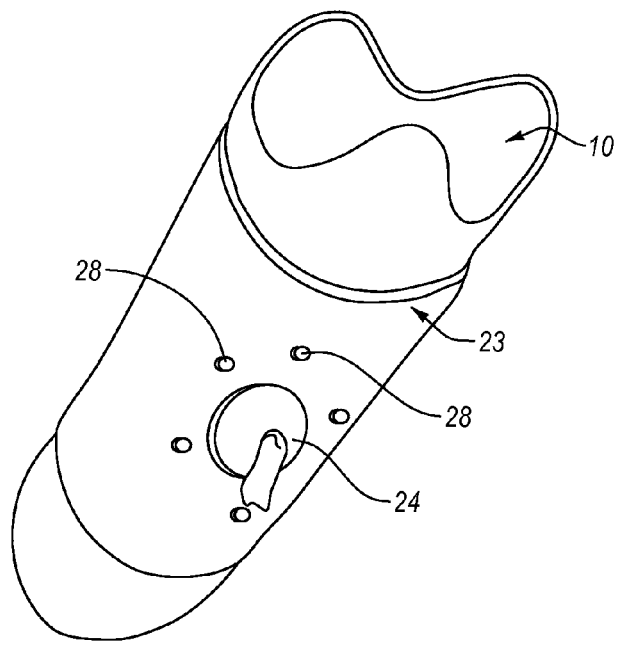
FIG. 6 is a perspective view of the vacuum suspension system of FIG. 1 having a covering with expulsion holes.

FIG. 6 illustrates an embodiment of the vacuum suspension system 20 having a covering 23 capable of serving as a second fluid regulator even when the covering 23 substantially covers the entire socket exterior. This is accomplished by expulsion holes 28 formed within the covering 23 at a location near the pump 24.

Figure 7A:
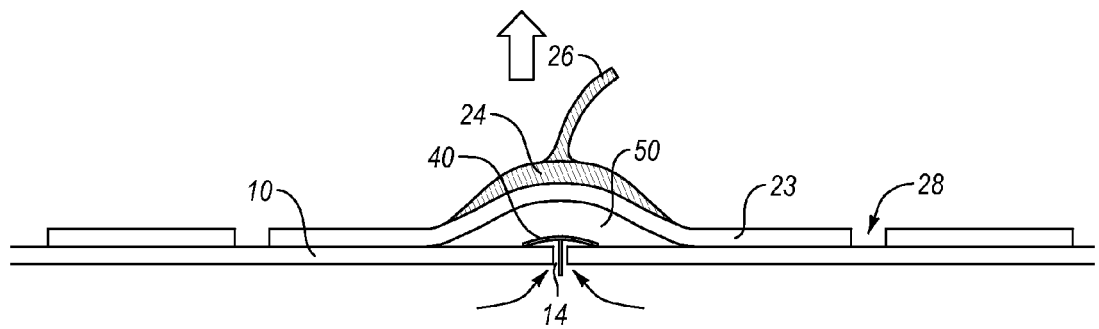
FIGS. 7(a) and 7(b) are cross-sectional views showing how the on-socket vacuum pump of FIG. 6 is operated.
Figure 7B:
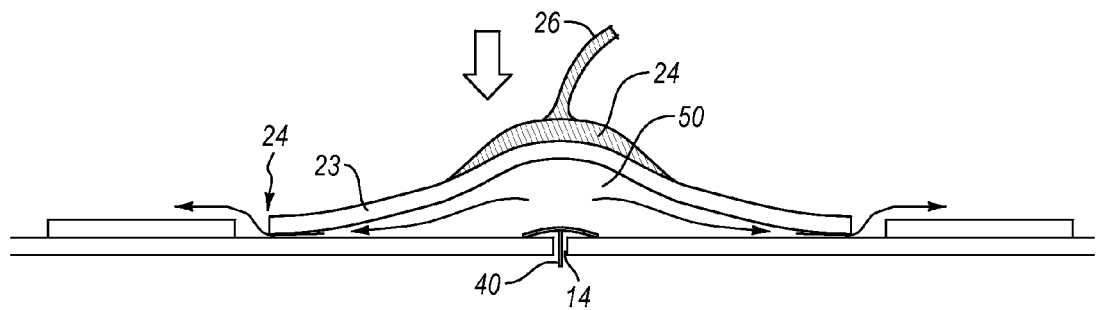

Air is drawn into the chamber 50 through valve 40 from the socket interior when the handle is pulled away from the socket 10 as shown in FIG. 7(a). Upon release of the handle 26, the covering 23 naturally returns it to its original position compressing the socket 10 due to its elasticity, during which the air collected within the chamber 50 is forced out through the corresponding expulsion holes 28 as shown in FIGS. 7(a) and 7(b).

Figure 8:
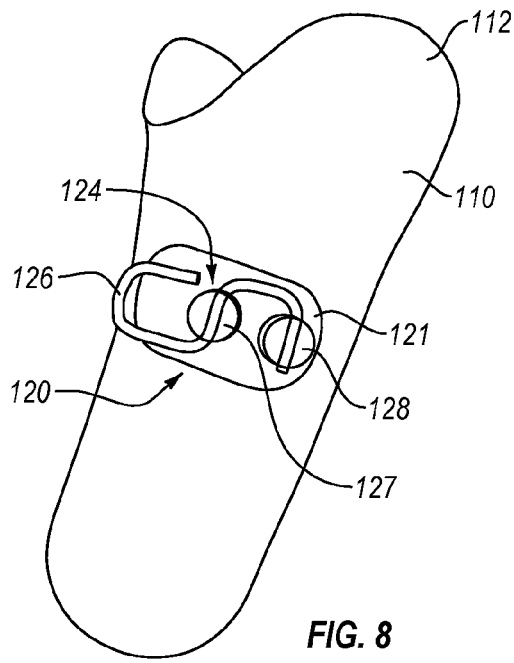
FIG. 8 is a perspective view of a vacuum suspension system secured to a prosthetic socket according to another embodiment of the disclosure.
Figure 9:
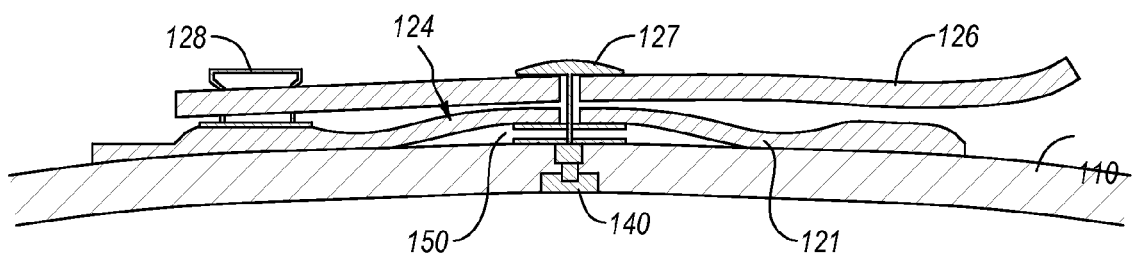
FIG. 9 is a detailed cross-sectional view of the vacuum suspension system according to FIG. 8.

As illustrated in FIGS. 8 and 9, another embodiment of the vacuum suspension system 120 includes a pump 124 formed by an elastic covering 121 attached directly to the exterior surface of a hard prosthetic socket 110. The covering may include at least one knob 127 formed thereon, with a latch 126 provided or embedded therein. A second knob 128 may be provided to help anchor the latch 126 to the covering 121, and to provide an abutment for a user to grip while pulling the latch during operation of the pump.

The outer periphery of the covering 121 is preferably adhered to the socket 110, and defines an air-tight chamber 150 therebetween. The covering 121 may be made from a flexible elastomer, such as polyurethane, to allow expansion of the chamber 150, and may be provided for attachment to the hard prosthetic socket 110. The covering 121 can be configured for an air-tight sealing engagement with the socket 110 by rolling its proximal end over the brim 112 of the socket as previously described in the first embodiment. Similar to the first embodiment, the socket 110 also includes a hole, as in FIG. 3 in the wall for receiving a fluid regulator 140, such as a one-way valve. The elastic covering 121 is preferably on the socket 110 in a position over the fluid regulator 140 so the chamber 150 is in fluid communication with the socket interior via the one-way valve.

The air differential within the socket interior is maintained by the air-tight seal created between the socket 110 and the liner 130. Pulling the latch 126 in a direction outwardly away from the socket elastically expands the size of the chamber 150 and increases its volume to define an air chamber. This process creates a vacuum effect over the valve 140 on the exterior surface of the socket 110. The negative pressure created within the air chamber during the inflation process releases the one-way valve on the socket to correspondingly draw out air from within the socket interior. The resulting increase of suction suspension helps hold the residual limb within the socket.

A second fluid regulator, such as a one-way valve, may be on the pump for expelling air from the chamber out into the environment. Emptying the collected air from the chamber causes it to elastically return to its original non-expanded state. This allows the patient to repeat pumping additional air out from the socket interior, as desired. It is also advantageous that the vacuum pump 124 can be attached to most existing prosthetic sockets and is easy to install. The hole 114 should first be drilled in the socket 110 for attaching a one-way valve 140 thereto. Subsequently, the pump 124 can be adhesively bonded over the valve to provide an air-tight seal.

It should further be appreciated that many variations of the latch 126 having different shapes and sizes can be used for manipulating the elastic covering 121 to operate the pump. Although such variations may differ in form, they perform substantially similar functions.

Figure 10:
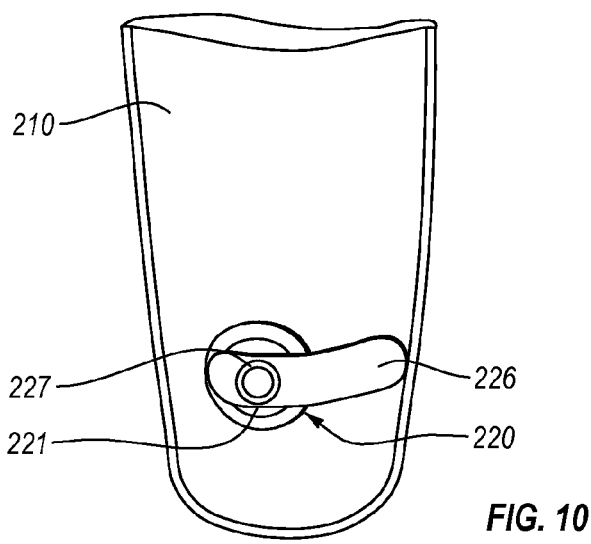
FIG. 10 is a front elevational view of a vacuum suspension system secured to prosthetic socket according to another embodiment.
Figure 11:
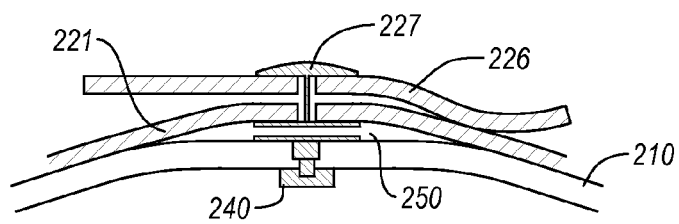
FIG. 11 is a detailed cross-sectional view of an on-socket vacuum pump according to another embodiment of the disclosure.

FIGS. 10 and 11 illustrate an embodiment of a vacuum suspension system 220 having a latch 226 connected to a single knob 227. When a user pulls the latch 226, the knob 227 is correspondingly lifted away from the exterior surface of the socket 210, expanding the elastic covering 221. This creates a vacuum effect over a valve 240 formed in the wall of the socket, which helps expel air out from within the socket interior.

Figure 12A:
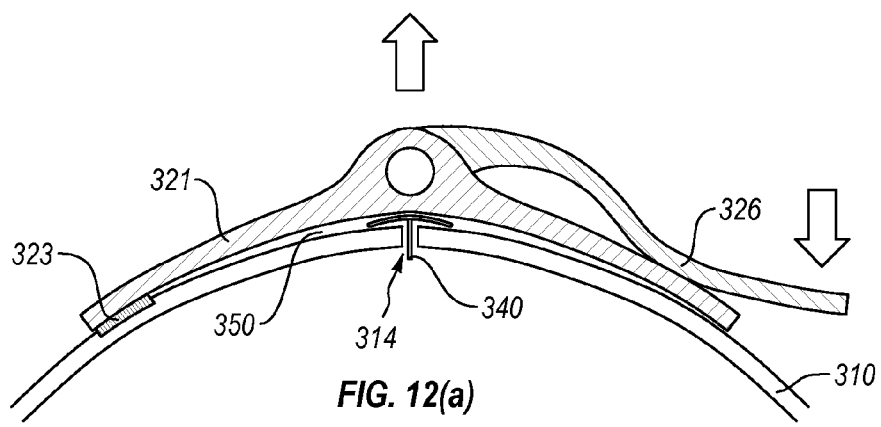
FIGS. 12(*a*) and 12(*b*) are cross-sectional views of the on-socket vacuum pump according to another embodiment of the disclosure.
Figure 12B:
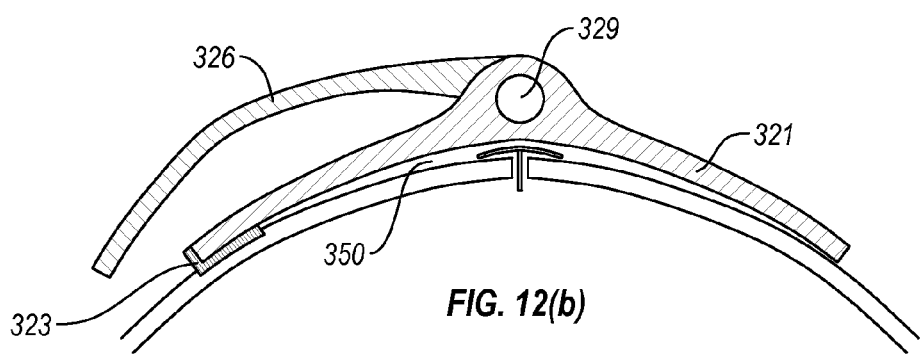
Figure 12C:
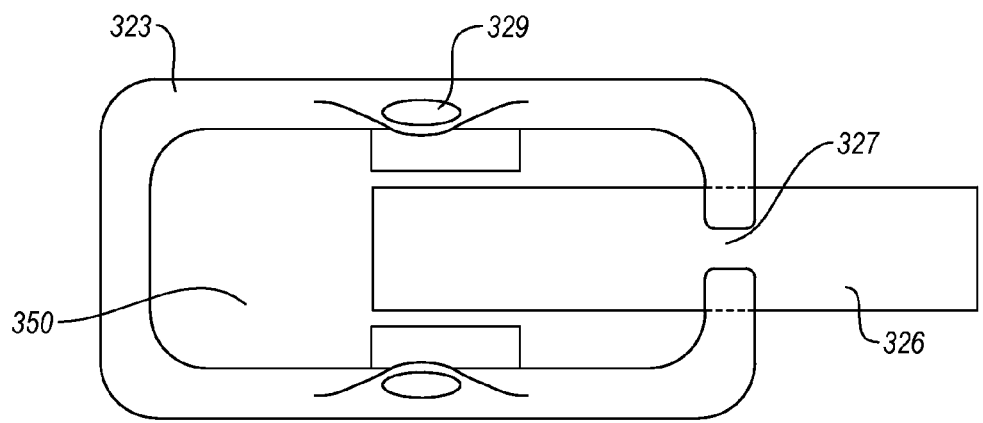

Alternatively, FIGS. 12(*a*) and 12(*b*) show a latch 326 connected to an elastic covering 321 by a swivel member 329, such as a hinge. The elastic covering 321 forms a sealing connection 323 with the socket exterior to define a chamber 350 having a variable volume therebetween. When the free end of the latch 326 is depressed toward the socket 310, the hinge portion is lifted and correspondingly acts to expand the chamber 350 to create a pump chamber for accumulating air, as illustrated in FIG. 12(*a*).

Similar to previous embodiments, the resulting pressure differential created within the pump chamber draws out air from within the socket interior through the hole 314 in the socket 310 via the fluid regulator 340. When the free end of the latch is subsequently lifted away from the socket, the pumping of air out from the socket interior ceases, as illustrated in FIG. 12(*b*). The accumulated air within the air chamber 350 can be expelled out into the environment through an opening 327 formed between the covering 321 and the socket exterior, and located under the latch 326 as shown in FIG. 12(*c*).

By providing a vacuum pump directly on the socket, pumping can easily be accomplished anytime during use. The pump can be operated when the socket is initially donned, during walking when additional pushing and pulling forces apply to the residual limb, or even when sitting immobile with no additional forces exerted on the limb. Since the pump has a low profile, there is less chance of it getting knocked off the socket or damaged because of it snagging or bumping into foreign objects. Its low profile ensures total control of the prosthetic device is not inhibited so that the patient can fully operate it as intended. Placing the vacuum pump directly on the socket does not make wearing the brace uncomfortable for the user. Securing the pump directly to the socket also advantageously decreases the likelihood that a patient might lose the pump during use.

Figure 13:
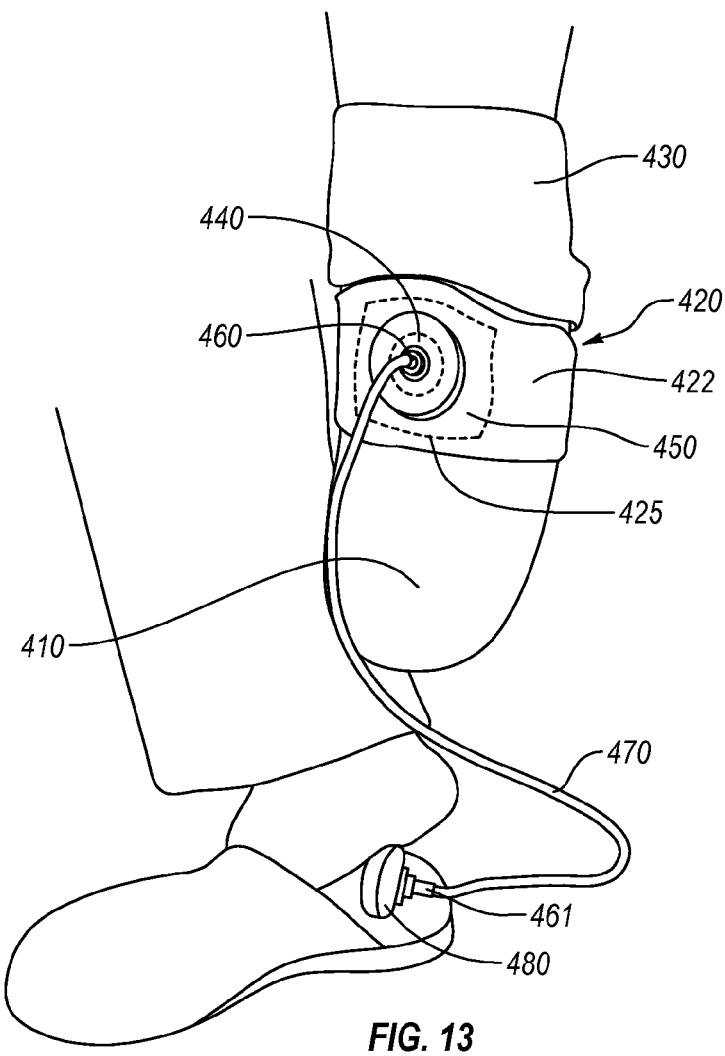
FIG. 13 is a perspective view of the embodiment of FIG. 14 illustrating how the on-socket vacuum pump is operated.

FIG. 13 shows another embodiment of the vacuum suspension system including a pump system 420. An elastic covering 422 is provided for attachment to a hard prosthetic socket for receiving a fluid regulator 440, such as a one-way valve. A chamber 425 having a variable volume is formed between the covering 422 and an exterior surface of the socket 410 so it is correspondingly placed over the fluid regulator 440. The chamber 425 is arranged such that it forms a substantially dome-like shape over the fluid regulator 440.

A first connecting portion 460 may be integrally formed on the covering 422 to provide fluid engagement between the chamber 425 and a tubular fluid conduit 470. The fluid conduit 470 is attached at one end to the first connecting portion 460, and is attached at its opposite end to a second connecting portion 461 for providing fluid engagement to a second pump 480. The pump 480 serves as a manual pump, such that when compressed, the air or fluid inside is expelled through the conduit 470 and into the chamber 425. This action causes the chamber 425 to inflate and form a dome-like shape protruding outwardly away from the socket 410 underneath the covering 422. The chamber 425 is maintained against the exterior surface of the socket by compression supplied by the covering 422.

The air differential within the socket interior is preferably maintained by a socket liner 430 that can be rolled at its proximal end over a brim of the socket 410 to make an air-tight seal. Inflating the chamber 425 creates a vacuum effect, which causes air to be drawn out through the valve 440 from the interior of the socket 410. This air is drawn into the air chamber 425 defined by the space created between the exterior of the socket and the chamber formed on the underside of the fully expanded dome-shaped chamber 450.

During use, the negative pressure created within the air chamber by the chamber 425 releases the one-way valve on the socket 410 to draw out air from within the socket interior. When the second pump 480 is disengaged, the air or fluid is returned to it from the chamber 425, causing the chamber to deflate. As the chamber returns to its initial pre-inflated state, the air drawn out from the socket interior into the chamber is expelled into the atmosphere either through expulsion holes formed on the covering 422 or from under the peripheral ends of the covering.

By providing the second pump 480 in fluid connection with the chamber, a pumping action can be manually employed by hand or activated automatically during ambulation. The second pump can be placed underneath the patient's prosthetic foot so that when pressure is naturally applied to the second pump by the patient's weight while walking, the vacuum pumping process occurs.

The pump 480 may be configured to fit in an area separate from the socket, such as in the insole of a shoe, within a foot cover, under a prosthetic foot, or in a specially designed pump chamber attached to a specific prosthetic foot. The second pump may be compressed due to the positive pressure created on it during the heel strike stage of walking, causing the air and/or fluid to be transported through the conduit into the chamber 425. This would advantageously allow a user to repeatedly pump any excess air out of the socket interior while walking for continuous suction suspension.

Figure 14:
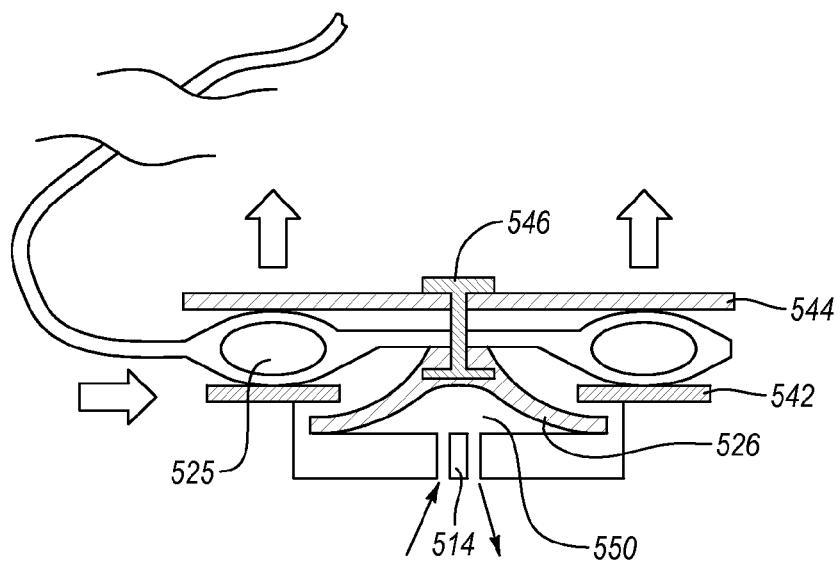
FIG. 14 is a detailed cross-sectional view illustrating a variation of the vacuum suspension system of FIG. 13.

Another embodiment of the chamber is in FIG. 14, where the bladder 525 is generally donut-shaped and secured between an inner plate 542 and may include a stiff outer shift plate by a fastening member 546. The fastening member 546 is further affixed to the socket by a flexible member 526, such as a rubber membrane, formed over a hole 514 in the socket and defining a chamber therebetween.

The outer shift plate 544 is lifted away from the socket as the donut-shaped bladder 525 expands due to the positive pressure introduced by a second pump preferably located under a prosthetic foot or within a foot cover. This causes the fastening member 546 to correspondingly expand the flexible member 526 and form an air chamber 550. The resulting pressure differential draws air out of the socket interior and into the air chamber 550. When the second pump is pumped with air and/or fluid into the chamber, the air chamber will return back to a zero volume stage and correspondingly push the air and/or fluid back to the second pump adjacent the user's foot so it is ready for the next compression.

Figure 15:
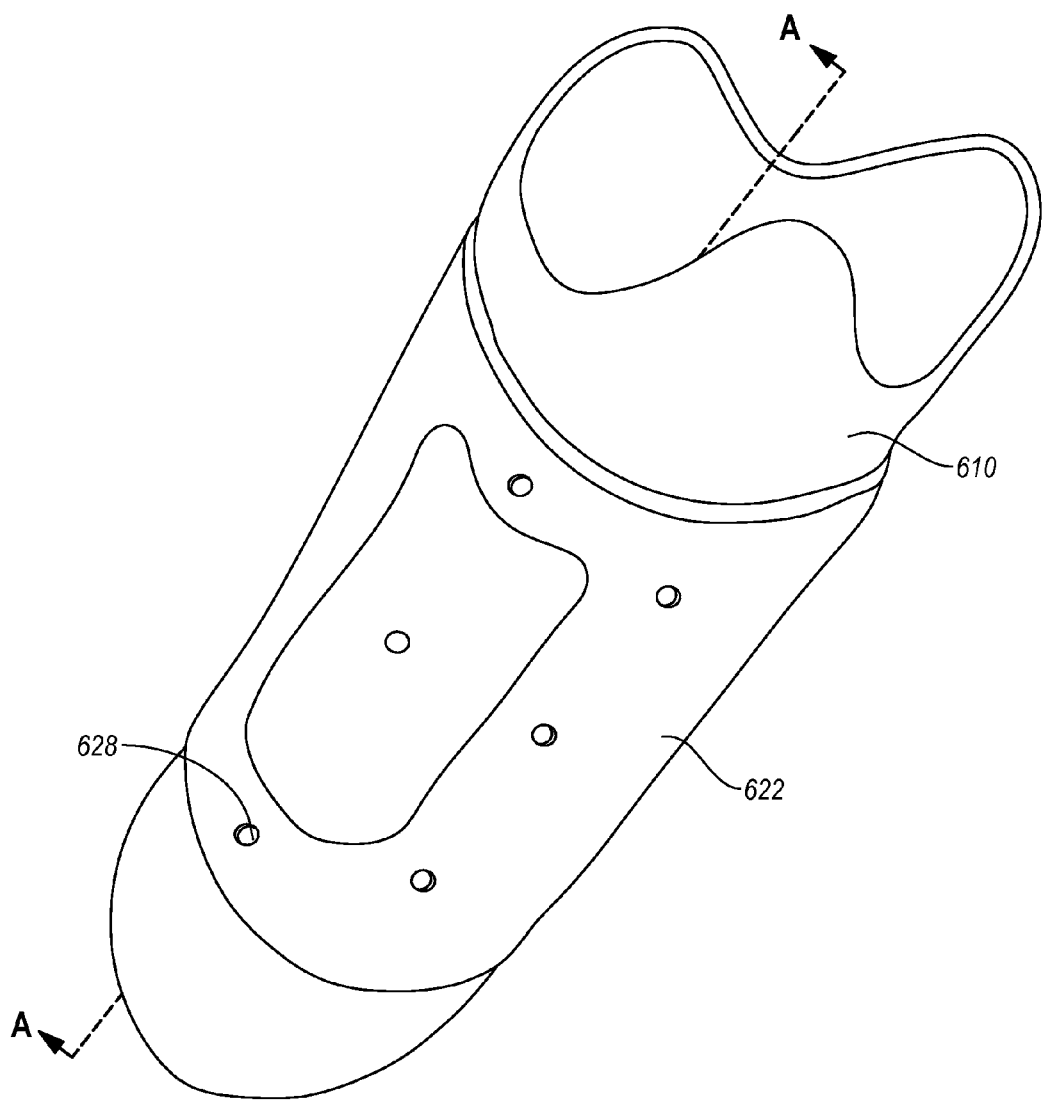
FIG. 15 is a perspective view of another embodiment of the vacuum suspension system of the present disclosure.
Figure 16:
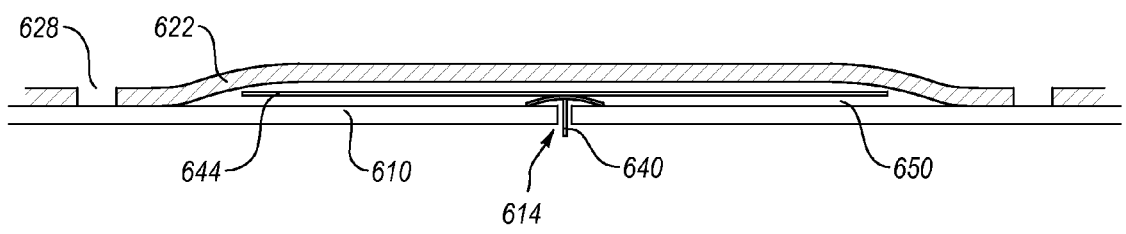
FIG. 16 is a detailed cross-sectional view of the vacuum suspension system of FIG. 15 along line A-A.

FIGS. 15 and 16 illustrate an embodiment of the vacuum suspension system that can secure a residual limb within a socket without a manually controlled pump. Instead, the socket 610 includes a hole 614 for receiving a fluid regulator 640, such as a one-way valve. A sealing covering 622 is provided over the exterior surface of the socket 610 to cover the fluid regulator 640. A shift plate 644 is preferably secured between the covering 622 and the socket 610 at a location covering the fluid regulator 640.

It should be appreciated that the plate may be sealed to the socket via compression applied by the covering, or it may be adhesively bonded to the covering. Walking and other weight-bearing activities help create suction suspension. As the residual limb is pushed further into the socket, air is displaced out through the valve, and as the limb is pulled out of the socket during the swing phase of walking, suction suspension on the limb occurs since the valve will not permit air to re-enter the socket.

The resulting limb movement further into the socket 610 acts to pump air out of the socket interior through the fluid regulator 640. The air is accumulated in a chamber defined by the space created between the plate 644 and the socket 610. As a wearer walks, the relative movement of the residual limb within the socket will repeatedly push excess air out from within the socket through the fluid regulator 640 and into the chamber 650. The air may then be expelled out into the environment as in the previous embodiments. The covering 622 may include expulsion holes 628 located adjacent to areas of the covering that form a sealing connection with the socket 610. These expulsion holes 628 allow the accumulated air within the chamber 650 to be released into the atmosphere.

The one-way valve 640 can also relieve a buildup of pressure when the liner-sheathed limb is first inserted into the socket 610. This prevents a positive air pressure inside the socket relative to the ambient air outside to permit donning the socket while still providing a snug fit for the limb. Easy donning is accomplished since air may be automatically expelled as the limb is inserted into the socket. This is because the volume of the limb displaces the volume of air inside the socket, forcing the remaining air out through the one-way valve. Any air expelled through the one-way valve cannot re-enter the socket through the same channel. The suspension fit of the limb within the socket can be preserved.

The invention claimed is:

1. A vacuum suspension system, comprising:
    a rigid socket defining a wall having exterior and interior surfaces, and an aperture extending between the exterior and interior surfaces, the socket having a closed distal end and an open proximal end, the socket forming an interior cavity defined by the interior surface;
    a fluid regulator provided at the aperture;
    a pump system including a pump and a covering for securing over the exterior surface of the socket and supporting the pump, the pump configured for placement proximate to the fluid regulator and arranged for drawing air from the socket through the aperture and operatively engaging the fluid regulator;
    a chamber having a variable volume and formed by a space defined between the exterior surface and an inner surface of the covering proximate to the pump;
    wherein the pump system includes a handle operatively connected to the fluid regulator and arranged for being adjusted for drawing air from the socket cavity;
    wherein the covering is arranged to permit escape of air from the chamber upon release of the handle, and forms a one-way valve with the exterior surface of the socket.

2. The vacuum suspension system of claim 1, wherein the pump system includes activation means for expanding and decreasing the volume of the chamber.

3. The vacuum suspension system of claim 1, wherein the covering is arranged to seal against the exterior surface of the socket and selectively prevent escape of air from an interface formed between the covering and the exterior surface.

4. The vacuum suspension system of claim 2, wherein the covering is air impermeable and seals against the exterior surface of the socket at least in an area proximate to and extending over the aperture.

5. The vacuum suspension system of claim 1, wherein the chamber is defined by a dome formed between the exterior surface of the socket and the inner surface of the covering.

6. The vacuum suspension system of claim 1, wherein the covering has at least one portion adapted to channel air from the chamber to the atmosphere.

7. A kit for a vacuum system for connection to a rigid socket having a wall defining exterior and interior surfaces, the socket defining an aperture extending between the exterior and interior surfaces, the socket having a closed distal end and an open proximal end, comprising:
    a fluid regulator arranged to be provided at the aperture;
    a pump configured for placement proximate to the fluid regulator and arranged for drawing air from the socket through the aperture and operatively engaging the fluid regulator;
    a covering for securing over the exterior surface of the socket and forming a chamber having a variable volume defined between the exterior surface and an inner surface of the covering proximate to the pump;
    wherein the pump includes a handle arranged for operating the fluid regulator and arranged for being adjusted for drawing air from the socket cavity;
    wherein the handle is generally elastic and returns to a predetermined first position both prior to and at release thereof, as the handle is pulled away from the exterior surface of the socket.

8. The kit of claim 7, wherein the covering is generally air impermeable and has a least a portion permit escape of air from the chamber to atmosphere.

9. A vacuum suspension system, comprising:
    a rigid socket defining a wall having exterior and interior surfaces, and an aperture extending between the exterior and interior surfaces, the socket having a closed distal end and an open proximal end, the socket forming an interior cavity defined by the interior surface;
    a fluid regulator provided at the aperture;
    a pump system including a pump and a covering for securing over the exterior surface of the socket and supporting the pump, the pump configured for placement proximate to the fluid regulator and arranged for drawing air from the socket through the aperture and operatively engaging the fluid regulator;

a chamber having a variable volume and formed by a space defined between the exterior surface and an inner surface of the covering proximate to the pump;
wherein the pump system includes a handle operatively connected to the fluid regulator and arranged for being adjusted for drawing air from the socket cavity;
wherein the handle is generally elastic and returns to a predetermined first position both prior to and at release thereof, as the handle is pulled away from the exterior surface of the socket.

10. A vacuum suspension system, comprising:

a rigid socket defining a wall having exterior and interior surfaces, and an aperture extending between the exterior and interior surfaces, the socket having a closed distal end and an open proximal end, the socket forming an interior cavity defined by the interior surface;
a fluid regulator provided at the aperture;
a pump system including a pump and a covering for securing over the exterior surface of the socket and supporting the pump, the pump configured for placement proximate to the fluid regulator and arranged for drawing air from the socket through the aperture and operatively engaging the fluid regulator;
a chamber having a variable volume and formed by a space defined between the exterior surface and an inner surface of the covering proximate to the pump;
wherein the covering is substantially more flexible than the exterior surface of the socket.

* * * * *